United States Patent
Ida et al.

(10) Patent No.: US 9,301,937 B2
(45) Date of Patent: *Apr. 5, 2016

(54) AMINO-ACID-CONTAINING MEDICINAL GRANULAR PREPARATION HIGHLY EASY TO TAKE

(75) Inventors: Mitsuyasu Ida, Mie (JP); Nobutaka Ninomiya, Mie (JP)

(73) Assignee: AJINOMOTO CO., INC., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 12/697,563

(22) Filed: Feb. 1, 2010

(65) Prior Publication Data

US 2010/0178350 A1    Jul. 15, 2010

Related U.S. Application Data

(63) Continuation of application No. PCT/JP2008/063763, filed on Jul. 31, 2008.

(30) Foreign Application Priority Data

Jul. 31, 2007  (JP) ................................ 2007-199875
Oct. 26, 2007  (JP) ................................ 2007-279550
Jun. 13, 2008  (JP) ................................ 2008-155594

(51) Int. Cl.
  *A61K 9/14*  (2006.01)
  *A23L 1/30*  (2006.01)
  *A61K 31/198*  (2006.01)
  *A23L 1/305*  (2006.01)
  *A61K 9/16*  (2006.01)

(52) U.S. Cl.
  CPC ............ *A61K 31/198* (2013.01); *A23L 1/3051* (2013.01); *A61K 9/16* (2013.01); *A61K 9/1617* (2013.01); *A61K 9/1635* (2013.01); *A61K 9/1682* (2013.01); *A23V 2002/00* (2013.01)

(58) Field of Classification Search
  None
  See application file for complete search history.

(56) References Cited

U.S. PATENT DOCUMENTS 4,675,339 A * 6/1987 Inoue et al. .................. 514/419
4,753,804 A * 6/1988 Iaccheri et al. ............... 424/491
6,264,989 B1 7/2001 Kato et al.
6,337,084 B1 * 1/2002 Stevens et al. ................ 424/442
2002/0168368 A1 11/2002 Kim
2005/0003015 A1 1/2005 Sakai et al.

FOREIGN PATENT DOCUMENTS

| CN | 1658862 A | 8/2005 |
|---|---|---|
| JP | 10-305518 | 11/1998 |
| JP | 10-305868 | 11/1998 |
| JP | 11-70607 | 3/1999 |
| JP | 11-092403 | 4/1999 |
| JP | 3233155 | 9/2001 |
| JP | 3259731 | 12/2001 |
| JP | 2002-145769 A | 5/2002 |
| JP | 2002-154958 A | 5/2002 |
| JP | 2003-519649 | 6/2003 |
| JP | 2003-212768 | 7/2003 |
| JP | 2004-075600 | 3/2004 |
| JP | 2004-339062 A | 12/2004 |
| JP | 2007-169264 | 7/2007 |
| JP | 2007-182411 | 7/2007 |
| JP | 2008-162955 | 7/2008 |
| WO | WO 2007/043363 | 4/2007 |

OTHER PUBLICATIONS

JP 2002-154958, english machine translation, publication date: May 28, 2002, Inventor: Takasu Kazuhiro, et al., pp. 1-7.*
Wikipedia, Mesh (scale), accessed Feb. 11, 2014, pp. 1-9.*
Japanese Office Action issued Mar. 12, 2013, in Japan Patent Application No. 2009-525448.
Extended European Search Report issued Jul. 17, 2013 in Patent Application No. 08 791 978.3.
Office Action issued Jun. 23, 2015, in Japanese Patent Application No. 2009-525448 (with English translation).
Japanese Office Action issued Feb. 17, 2015, in Japan Patent Application No. 2014-024341(w/ English Translation).

* cited by examiner

*Primary Examiner* — Dennis J Parad
*Assistant Examiner* — Lyndsey Beckhardt
(74) *Attorney, Agent, or Firm* — Oblon, McClelland, Maier & Neustadt, L.L.P.

(57) ABSTRACT

The present invention aims to provide an amino acid-containing granule preparation improved in the ease of taking medication than conventional products, which disintegrates rapidly. The amino acid-containing granule preparation of the present invention containing granules having a maximum particle size of substantially not more than 1000 μm and a bulk density of not less than 0.57 g/mL markedly improves ease of taking medication without impairing disintegration property, as compared to conventional amino acid-containing granule preparations.

9 Claims, No Drawings

AMINO-ACID-CONTAINING MEDICINAL GRANULAR PREPARATION HIGHLY EASY TO TAKE

TECHNICAL FIELD

The present invention relates to an amino acid-containing granule preparation highly easy to take.

BACKGROUND ART

Conventional amino acid-containing granule preparations, particularly some of branched chain amino acid-containing granule preparations, have problems in that granules are large, cause a sensation of foreign body in the mouth to degrade ease of ingestion, or a large volume thereof per ingestion dose is felt bulky in the mouth and difficult to swallow, and the like.

The correlation between volume and ease of taking medication is said to be particular strong. When the particle size of granules is reduced to decrease the sensation of foreign body during ingestion, the volume increases and granules become bulky in the mouth during ingestion, making swallowing difficult. A volume reduction technique for branched chain amino acid by a stirring granulation method has been developed and patented (patent document 1); however, further improvement in the ease of taking medication has been desired.

Consolidation during granulation in an attempt to decrease the volume promotes granulation, which partly enlarges the granules. As a result, the feeling on the tongue may be degraded, the sensation of foreign body may increase during ingestion, and disintegration of granules may decrease, which in turn may lower absorbability. In addition, uncomfortableness during taking medication may cause low medication compliance.

Therefore, the development of an amino acid-containing granule preparation has been desired, which is small in volume and disintegrates rapidly without a feeling on the tongue and a sensation of foreign body.

patent document 1: Patent Publication No. 3368898

DISCLOSURE OF THE INVENTION

Problems to be Solved by the Invention

The present invention aims to provide an amino acid (particularly, branched chain amino acid)-containing granule preparation improved in the ease of taking medication than conventional amino acid-containing granule preparations, which disintegrates rapidly.

Means of Solving the Problems

The present inventors have conducted intensive studies in view of the above-mentioned problems, and found that an amino acid (particularly, branched chain amino acid)-containing granule preparation comprising granules having a maximum particle size of not more than 1000 μm and a bulk density of not less than 0.57 g/mL is improved in the ease of taking medication than conventional amino acid-containing granule preparations and is not impaired in the disintegration property, which resulted in the completion of the present invention.

Accordingly, the present invention provides the following.

[1] A granule preparation comprising an amino acid, wherein the granule has a maximum particle size of substantially not more than 1000 μm and a bulk density of not less than 0.57 g/mL.

[2] The granule preparation of [1], wherein the amino acid is at least one kind selected from isoleucine, leucine and valine.

[3] The granule preparation of [1], wherein the amino acid comprises isoleucine, leucine and valine.

[4] The granule preparation of [3], wherein the weight ratio of isoleucine, leucine and valine is 1:1.5-2.5:0.8-1.7.

[5] The granule preparation of [1], wherein the bulk density is not less than 0.59 g/mL.

[6] A pharmaceutical product or food, which is filled with 1-10 g of the granule preparation of [1] per one ingestion dose.

Effect of the Invention

The amino acid-containing granule preparation of the present invention comprises granules having a maximum particle size of substantially not more than 1000 μm and a bulk density of not less than 0.57 g/mL, and therefore, can reduce the volume thereof. As a result, since the amino acid-containing granule preparation of the present invention can be taken without an uncomfortable feeling and a sensation of foreign body, it can enhance medication compliance. While the amino acid-containing granule preparation of the present invention is consolidated to reduce its volume, it disintegrates rapidly.

BEST MODE FOR CARRYING OUT THE INVENTION

The present invention is explained in detail in the following.

The present invention relates to an amino acid (particularly, branched chain amino acid)-containing granule preparation (hereinafter to be simply referred to as the "granule preparation of the present invention").

In the present invention, the "granule preparation" refers to the granule in the context of the Japanese Pharmacopoeia, 15th Edition (hereinafter to be simply referred to as "the Japanese Pharmacopoeia").

The "amino acid", which is the active ingredient of the present invention, includes amino acids constituting a protein and those not constituting a protein. Examples of the amino acid constituting a protein include aliphatic amino acid (glycine, alanine), branched chain amino acid (isoleucine, leucine, valine), hydroxyamino acid (serine, threonine), acidic amino acid (aspartic acid, glutamic acid), amide amino acid (asparagine, glutamine), basic amino acid (lysine, hydroxylysine, arginine, histidine), sulfur amino acid (cysteine, cystine, methionine), aromatic amino acid (phenylalanine, tyrosine), heterocyclic amino acid (tryptophan, histidine) and imino acid (proline, 4-hydroxyproline). Examples of the amino acid not constituting a protein include, but are not limited to, β-alanine, γ-aminobutyric acid, homocysteine, ornithine, 5-hydroxytryptophan, 3,4-dihydroxyphenylalanine, triiodothyronine, thyroxine and the like.

Examples of the branched chain amino acid contained in the granule preparation of the present invention include isoleucine, leucine and valine, which are generally used for pharmaceutical products, foods and the like.

Any of L-form, D-form and DL-form of the amino acid can be used. Preferred are L-form and DL-form, and more preferred is L-form.

In addition, the amino acid can be used in the form of not only a free form but also a salt. In the present invention, the amino acid is a concept encompassing both the free form and the salt.

Examples of the salt include acid addition salt, a salt with a base and the like, and a pharmaceutically acceptable salt of amino acid is preferably selected.

Examples of an acid to be added to an amino acid to form a pharmaceutically acceptable salt include inorganic acids such as hydrogen chloride, hydrogen bromide, sulfuric acid, phosphoric acid and the like; organic acids such as acetic acid, lactic acid, citric acid, tartaric acid, maleic acid, fumaric acid, monomethylsulfuric acid and the like.

Examples of a base that forms a pharmaceutically acceptable salt of an amino acid include hydroxide or carbohydrate of a metal such as sodium, potassium, calcium and the like, inorganic bases such as ammonia and the like; organic bases such as ethylenediamine, propylenediamine, ethanolamine, monoalkylethanolamine, dialkylethanolamine, diethanolamine, triethanolamine and the like.

In one embodiment, the granule preparation of the present invention contains at least one kind of branched chain amino acid selected from isoleucine, leucine and valine, and preferably contains isoleucine, leucine and valine at the same time. When the granule preparation of present invention contains isoleucine, leucine and valine at the same time, the mixing ratio of the three kinds of branched chain amino acids is within the range of, for example, 1:1.5-2.5:0.8-3, more preferably 1:1.5-2.5:0.8-1.7, particularly preferably 1:1.9-2.2: 1.1-1.3, in weight ratio.

The granule preparation of the present invention is characterized in that the granules in the preparation have a bulk density of not less than 0.57 g/mL, preferably not less than 0.59 g/mL, more preferably not less than 0.62 g/mL, and preferably not more than 0.75 g/mL.

The bulk density can be measured according to the method of bulk specific gravity described in the appendix (regulations) vinyl chloride resin test method of the Japanese Industrial Standards, plastic-vinyl chloride homopolymer and copolymer (PVC)—Part 2: How to produce test piece and how to measure various properties (standard number JISK6720-2) (hereinafter to be referred to as the method described in JIS).

In addition, it can be measured according to a method including dropping the measurement granules by gently shaking them from about 15 cm above, measuring the granule mass filled in a 100 mL container, and calculating bulk density from the granule mass (hereinafter to be referred to as a convenient method). The bulk density obtained by the method described in JIS and that obtained by the convenient method are almost the same. Even when a difference exists, as long as the bulk density measured according to either method is within the above-mentioned range, the granules can be contained in the granule preparation of the present invention.

Moreover, the granule preparation of the present invention is characterized in that the granules in the preparation have a maximum particle size of substantially not more than 1000 μm, preferably substantially not more than 850 μm, more preferably substantially not more than 710 μm, and preferably not less than 355 μm.

The "substantial" in the present application shows that granules having a particle size exceeding 1000 μm (preferably 850 μm, more preferably 710 μm) to the extent free of an uncomfortable feeling and a sensation of foreign body during ingestion. The extent free of an uncomfortable feeling and a sensation of foreign body during ingestion is, for example, when granules having a particle size greater than 1000 μm and not more than 1400 μm are contained in not more than 1% (when the maximum particle size is substantially 1000 μm), when granules having a particle size greater than 850 μm and not more than 1000 μm are contained in not more than 1% (when the maximum particle size is substantially 850 μm), when granules having a particle size greater than 710 μm and not more than 850 μm are contained in not more than 1% (when the maximum particle size is substantially 710 μm) and the like.

To meet the Japanese Pharmacopoeia granule particle size standard, granules having a particle size of not more than 355 μm are contained in not more than 15%.

The measurement method of the maximum particle size is described in the following.

Stainless sieves with diameter 20 cm and aperture 1400, 1000, 850, 710, 600, 500, 400 and 355 μm and a tray are used. The tray is set at the bottom, and sieves are set on one another in such an order that a sieve with the smallest apertures is placed at the bottom. Measurement granules (about 50 g) are placed on the uppermost sieve (1400 μm), and shaken with a rotap sieve shaker for 5 min. After shaking, the granule mass on each sieve is measured and the particle size distribution (%) based on the on-sieve mass is calculate. The aperture at which the aforementioned particle size distribution based on the on-sieve mass less the particle size distribution based on the on-sieve mass of granules free of an uncomfortable feeling and a sensation of foreign body during ingestion is 0% is taken as the maximum particle size. Tests can be performed by changing the sieve aperture as appropriate.

The granule preparation of the present invention can be obtained by granulation according to a known granulation method (e.g., stirring granulation method, extrusion granulation method, fluidized bed granulation method, crushing granulation method etc.). In addition, granulated granules can be sieved by a known sieve method (e.g., impact sieve method, grinding sieve method, pressing sieve method, screening method etc.) which are used singly or in combination. Among the aforementioned methods, the stirring granulation method or extrusion granulation method, and grinding sieve method and screening method are preferably used in combination from the aspects of consolidation and control of the range of particle size distribution.

Granules with the aforementioned bulk density can be obtained by the aforementioned granulation methods. Preferable granulation conditions are described in patent publication No. 3368898 and granules having a high bulk density can be obtained, for example, by adding an acid. The acid is preferably citric acid, malic acid, tartaric acid, acetic acid, carbonic acid, phosphoric acid, hydrochloric acid or the like, and is appropriately added within the range of 0.1-5% by mass. These acids may be added singly as an aqueous solution, or may be used together with other additives such as a binder. Those of ordinary skill in the art can appropriately control granulation conditions and can obtain granules having the aforementioned bulk density and maximum particle size depending on the selection of apparatuses and setting of the conditions.

In addition, the particle size of the granules can also be determined according to the sieving conditions, and those of ordinary skill in the art can appropriately control the conditions for sieving by the aforementioned sieving methods. The conditions for screening methods are exemplified below. The setting of the aperture of a sieving machine is 355 μm and 1000 μm, preferably 400 μm and 850 μm, more preferably 400 μm and 710 μm. In addition, the number of passage through a sieving machine is not limited. Those of ordinary skill in the art can obtain granules having an objective particle size by appropriately controlling the setting of the numerical value of the aperture of the sieving machine, the number of passage through a sieving machine, change of the filtering mechanism of the sieving machine and the like.

The granule preparation of the present invention may be granules obtained using the granulation step or sieving step alone, namely, those obtained using a granulating machine or milling machine alone. Alternatively, when the maximum particle size and bulk density of granules in a preparation are within the above-mentioned ranges, they may be used as a final granule preparation. In this case, preferable granulating machine includes a high shear granulator (e.g., FS-GS-65JED (manufactured by Fukae Powtec.)), an extrusion granulating machine (e.g., pelleter double EXD-100 (manufactured by Fuji Paudal Co., Ltd.)), a crushing granulating machine (e.g., Roller Compactor MP90×30 (manufactured by TURBO KOGYO CO., LTD.)) and a fluid bed granulator (e.g., FLO-15 (manufactured by Freund Corporation)), and preferable milling machines are a grinding milling machine (e.g., Roll Granulator GRN-T54S (manufactured by NIPPON GRANULATOR CO., LTD.)), a pressing milling machine (e.g., COMIL QC-197S (manufactured by POWREX CORPORATION)), and an impact milling machine (e.g., new speed mill ND-30 (manufactured by OKADA SEIKO CO., LTD.)).

Using a high speed mixer FS-GS-65-JED, granulation is preferably performed at agitator: 50-200 rpm (preferably 90-150 rpm), chopper: 1000-3600 rpm (preferably 3000-3600 rpm), granulation time: 10-50 min (preferably 22-42 min). Using a HIGH FLEX GRAL HF-GS-65-JE, granulation is preferably performed at agitator: 50-250 rpm (preferably 90-200 rpm), chopper: 1000-2500 rpm (preferably 1500-2500 rpm), granulation time: 10-50 min (preferably 15-35 min). In the case of an agitation granulator, preferable granulation conditions vary depending on the apparatus; however, those of ordinary skill in the art can control conditions as appropriate.

In addition, the granule preparation of the present invention may be coated granules with coating for the object of taste masking, flavoring, coloring and the like, or when the maximum particle size and bulk density of granules in a preparation are within the above-mentioned ranges, they may be used as a final granule preparation. Granules obtained by a granulation step or a sieving step may be coated for the aforementioned objects. To be specific, coating may be performed after adjusting the particle size and bulk density by sieving and the like, or adjustment by sieving and the like may be performed after coating, and the maximum particle size and bulk density at the time of administration only need to be within the above-mentioned ranges. Coating can be performed according to a known method, such as spray coating method, fluidized bed coating method, pan coating method, rotor coating method and the like. Among the above-mentioned methods, a fluidized bed coating method and a rotor fluidized bed coating method are preferable from the aspects of easy application to granule preparations and formation of a uniform coating film. Coating can be performed by using, for example, fluid bed granulator FLO-15 (manufactured by Freund Corporation), fluidized bed granulating coating machine GPCG-60 (manufactured by POWREX CORPORATION), fine particle coating machine MP-25SFP (manufactured by POWREX CORPORATION), rotor fluid bed granulator SFC-5 (manufactured by Freund Corporation) and the like.

The granule preparation of the present invention is useful as a pharmaceutical product, food and the like, and is particularly useful for medical use. Examples of the administration subject include mammals (e.g., human, mouse, rat, hamster, rabbit, cat, dog, bovine, sheep, monkey etc.) and the like.

When the granule preparation of the present invention is a pharmaceutical product, it generally contains an amino acid and a carrier. The carrier is not particularly limited as long as it is a pharmaceutically acceptable carrier, and is exemplified by the below-mentioned substances for preparation (excipient, solvent etc.).

The pharmaceutical product can contain, when necessary for preparation, pharmacologically acceptable various pharmaceutical products or food as substances for preparation (auxiliary etc.). Examples of the substance for preparation include excipient, diluent, additive, disintegrant, binder, coating agent, lubricant, sliding agent, gliding agent, flavoring agent, sweetening agent, solubilizer, solvent and the like. Furthermore, specific examples of the substance for preparation include magnesium carbonate, titanium dioxide, lactose, mannitol and other saccharides, talc, milk protein, gelatin, starch, cellulose and a derivative thereof, animal and vegetable oil, polyethylene glycol, and solvent, for example, sterile water and monovalent or polyvalent alcohol, for example, glycerol and the like.

In addition, a coating agent to be used for coating can also contain various kinds of pharmacologically acceptable substances for preparation. Examples of the substance for preparation include binder, sweetening agent, acidulant, perfume and flavor, and coloring agent, which are more specifically hydroxypropylcellulose, ethylcellulose, aminoalkylmethacrylate copolymer E, polyvinylpyrrolidone, polyvinyl alcohol, aspartame, saccharin sodium, citric acid, ascorbic acid, tartaric acid, l-menthol, grapefruit essence, red ferric oxide, Food Blue No. 1, Food Red No. 3 and the like. The form of the coating agent may be a coating liquid or a solid sheet.

In addition, it is possible to provide the granule preparation of the present invention as food and drink such as food with health claims and the like prescribed by the Health, Labour and Welfare Ministry, and the food with health claims includes foods with a label indicating its particular use, particularly food for specified health uses, food with nutrient function claims and the like.

Moreover, the granule preparation of the present invention can be utilized as a dietary supplement. The dietary supplement in the present invention includes not only those ingested as foods but also those ingested to aid the nutrition, and nutritional supplement, supplement (particularly dietary supplement) and the like are also included therein.

One embodiment of the present invention is a pharmaceutical product or food filled with preferably 1-10 g, more preferably 3-5 g, of the above-mentioned granule preparation per ingestion dose. Such embodiment further clarifies the usefulness of the granule preparation of the present invention. In other words, when such volume of a pharmaceutical product or food is ingested at once, ease of taking medication is extremely important and becomes a factor that directly influences medication compliance and the like. Using the granule preparation of the present invention wherein granules having a large particle size are reduced and the size of granules is the same, a packaged product of a pharmaceutical product or food, which is easier to take even when the volume and amount are the same as those of packaged goods of existing granule preparations, can be obtained, and improvement of medication compliance at such volume can be expected.

As the package of a granule preparation, packaging materials and packaging methods generally used for packaging of pharmaceutical products and foods can be used. For example, divided packaging, stick packaging and the like can be used. As the packaging material, aluminum sheet (e.g., poly(ethylene terephthalate)+aluminum+polyethylene), and the packaging materials described in JP-A-10-305518, JP-A-10-305868 and JP-A-11-70607 and the like can be used. In addition, for filling during stick packaging, a stick fill packaging machine used generally can be employed.

The present invention is explained in detail in the following by referring to Examples, which are not to be construed as limitative.

EXAMPLES

Production Example 1

Three kinds of branched chain amino acids (isoleucine:leucine:valine=1:2:1.2 by weight ratio, 13.92 kg) were placed in a high shear granulator (FS-GS-65JED, manufactured by Fukae Powtec Co. Ltd.) and granulated under conditions of agitator (100 rpm) and chopper (2600 rpm) for 30 min using the binding solution of Table 1. The obtained granulated material was dried in a fluid bed granulator (FLO-15, manufactured by Freund Corporation) at a charge air temperature of 80° C. to give granules having a bulk density of 0.60 g/mL. The granules are passed through a sieving machine with aperture of 1000 μm, and granules on a 1000 μm sieve are applied to a milling machine (ND-02S, manufactured by OKADA SEIKO CO., LTD.). The granules under the 1000 μm sieve and the sieved granules were passed through a 355 μm aperture sieving machine to give final granules. The final granules had a bulk density of 0.59 g/mL and a maximum particle size of less than 1000 μm according to a convenient method. The formulation of the preparation is shown in Table 1.

TABLE 1

| | Name | Amount [kg] |
|---|---|---|
| Starting material | branched chain amino acid | 13.92 |
| Binding solution | povidone | 0.139 |
| | polyvinyl alcohol | 0.115 |
| | tartaric acid | 0.070 |
| | saccharine sodium | 0.059 |
| | purified water | 2.3 |

Production Example 2

Three kinds of branched chain amino acids (isoleucine:leucine:valine=1:2:1.2 by weight ratio, 13.92 kg) are placed in a high shear granulator (FS-GS-65JED, manufactured by Fukae Powtec Co. Ltd.) and granulated under conditions of agitator (127 rpm) and chopper (2000 rpm) for 21 min using the binding solution of Table 1. The obtained granulated material is dried in a fluid bed granulator (FLO-15, manufactured by Freund Corporation) at a charge air temperature of 80° C. to give granules. The granules are passed through a sieving machine with aperture of 850 μm, and granules on a 850 μm sieve are applied to a milling machine (GRN-T54S, manufactured by NIPPON GRANULATOR CO., LTD., roll pitch 4 mm, 2 mm, 1 mm, 0.6 mm). The granules under the 850 μm sieve and the sieved granules are passed through a 355 μm aperture sieving machine to give final granules. The final granules have a bulk density of 0.60 g/mL and a maximum particle size of less than 850 μm according to a convenient method.

Production Example 3

Three kinds of branched chain amino acids (isoleucine:leucine:valine=1:2:1.2 by weight ratio, 13.92 kg) are placed in a high shear granulator (FS-GS-65JED, manufactured by Fukae Powtec Co. Ltd.) and granulated under conditions of agitator (127 rpm) and chopper (2000 rpm) for 21 min using the binding solution of Table 1. The obtained granulated material is dried in a fluid bed granulator (FLO-15, manufactured by Freund Corporation) at a charge air temperature of 80° C. to give granules. The granules are passed through a milling machine with aperture of 850 μm, and granules on a 850 μm sieve are applied to a milling machine (ND-02S, manufactured by OKADA SEIKO CO., LTD.). The granules under the aperture 850 μm sieve and sieved granules are fed in a fluidized bed granulator (FLO-15, manufactured by Freund Corporation), and the coating solution of Table 2 (2.843 kg) is sprayed for coating. The granules are passed through a sieving machine with aperture of 850 μm, and granules on a 850 μm sieve are applied to a milling machine (GRN-T54S, manufactured by NIPPON GRANULATOR CO., LTD., roll pitch 4 mm, 2 mm, 1 mm, 0.6 mm). The granules under the 850 μm sieve and the sieved granules were passed through a 355 μm aperture sieving machine to give final granules. The final granules had a bulk density of 0.60 g/mL and a maximum particle size of less than 850 μm according to a convenient method.

TABLE 2

| | Name | Amount [kg] |
|---|---|---|
| Coating solution | povidone | 0.143 |
| | purified water | 2.7 |

Experimental Example 1

Granules were adjusted in the range of particle size distribution by a screening method, and model granules in compliance with the particle size standard of the Japanese is Pharmacopoeia, Granules, were prepared by excluding granules having a certain level of particle size or above. The model granules were administered to the panelists for evaluation. The bulk density was measured by a convenient method.

Sensory Evaluation Example

Test subjects: four individuals in their 30s and 40s

Evaluation method: The test granules were taken with a half cup of water (about 100 mL). After ingestion, the granules were evaluated for the volume, ease of swallowing and sensation of foreign body. Five-stage evaluation was performed wherein "small volume", "easily swallowed" and "less sensation of foreign body", which indicate comfortable ingestion, was 5 points, and "large volume", "difficult to swallow" and "high sensation of foreign body", which indicate uncomfortable ingestion, was 1 point. The average of each item was obtained and evaluated according to x: 1.0 point≤average<2.0 points, Δ: 2.0 points≤average<3.0 points, ○: 3.0 points≤average<4.0 points, and ⊙: 4.0 points≤average≤5.0 points.

In addition, a disintegration test was performed. For the evaluation, a disintegration time of 15 min or less was ⊙, 15 min<disintegration time≤30 min was ○, 30 min<disintegration time≤60 min was Δ, and longer than 60 min was x.

The results are shown in Table 3.

TABLE 3

| Ex. | Mass [g] | Particle size distribution and bulk density | Sensation of foreign body | Volume | Easiness of swallowing | Disintegration |
|---|---|---|---|---|---|---|
| Ex. 1 | 4.11 | Amount of granules on 710 μm 0%<br>Amount of granules on 600 μm 19%<br>Amount of granules on 500 μm 70%<br>Amount of granules on 400 μm 94%<br>Amount of granules on 355 μm 100%<br>bulk density 0.59 g/mL | ⊙ | ○ | ○ | ⊙ |
| Ex. 2 | 4.11 | Amount of granules on 710 μm 0%<br>Amount of granules on 600 μm 48%<br>Amount of granules on 500 μm 100%<br>bulk density 0.59 g/mL | ○ | ○ | ○ | ⊙ |
| Ex. 3 | 4.11 | Amount of granules on 1000 μm 0%<br>Amount of granules on 850 μm 29%<br>Amount of granules on 700 μm 63%<br>Amount of granules on 600 μm 92%<br>Amount of granules on 500 μm 100%<br>bulk density 0.59 g/mL | ○ | ○ | ○ | ⊙ |
| Ex. 4 | 4.11 | Amount of granules on 710 μm 0%<br>Amount of granules on 600 μm 19%<br>Amount of granules on 500 μm 70%<br>Amount of granules on 400 μm 94%<br>Amount of granules on 355 μm 100%<br>bulk density 0.62 g/mL | ⊙ | ○ | ○ | ⊙ |
| Com. Ex. 1 | 4.11 | Amount of granules on 1700 μm 0%<br>Amount of granules on 1400 μm 5%<br>Amount of granules on 1000 μm 13%<br>Amount of granules on 850 μm 61%<br>Amount of granules on 700 μm 78%<br>Amount of granules on 600 μm 90%<br>Amount of granules on 500 μm 100%<br>bulk density 0.59 g/mL | X | Δ | Δ | ⊙ |
| Com. Ex. 2 | 4.11 | Amount of granules on 710 μm 0%<br>Amount of granules on 600 μm 19%<br>Amount of granules on 500 μm 70%<br>Amount of granules on 400 μm 94%<br>Amount of granules on 355 μm 100%<br>bulk density 0.50 g/mL | ○ | Δ | Δ | ⊙ |

Experimental Example 2

Granules were adjusted in the range of particle size distribution by a screening method, and model granules in compliance with the particle size standard of the Japanese Pharmacopoeia, Granules, were prepared by excluding granules having a certain level of particle size or above. The model granules were administered to the panelists for evaluation. The bulk density was measured by the method described in JIS.

Sensory Evaluation Example

Test subjects: two individuals in their 40s
Evaluation method: The test granules were taken with a half cup of water (about 100 mL). After ingestion, the granules were evaluated for the volume, ease of swallowing and sensation of foreign body. Five-stage evaluation was performed wherein "small volume", "easily swallowed" and "less sensation of foreign body", which indicate comfortable ingestion, was 5 points, and "large volume", "difficult to swallow" and "high sensation of foreign body", which indicate uncomfortable ingestion, was 1 point. The average of each item was obtained and evaluated according to x: 1.0 point≤average<2.0 points, Δ: 2.0 points≤average<3.0 points, ○: 3.0 points≤average<4.0 points, and ⊙: 4.0 points≤average≤5.0 points.

In addition, a disintegration test was performed. For the evaluation, a disintegration time of 15 min or less was ⊙, min<disintegration time≤30 min was ○, 30 min<disintegration time≤60 min was Δ, and longer than 60 min was x.

The results are shown in Table 4.

TABLE 4

| Ex. | Mass [g] | Particle size distribution and bulk density | Sensation of foreign body | Volume | Easiness of swallowing | Disintegration |
|---|---|---|---|---|---|---|
| Ex. 5 | 4.11 | Amount of granules on 710 μm 0%<br>Amount of granules on 600 μm 20%<br>Amount of granules on 500 μm 70%<br>Amount of granules on 400 μm 95%<br>Amount of granules on 355 μm 100%<br>bulk density 0.57 g/mL | ○ | ○ | ○ | ⊙ |
| Ex. 6 | 4.11 | Amount of granules on 710 μm 0%<br>Amount of granules on 600 μm 50%<br>Amount of granules on 500 μm 100%<br>bulk density 0.57 g/mL | ○ | ○ | ○ | ⊙ |

TABLE 4-continued

| Ex. | Mass [g] | Particle size distribution and bulk density | Sensation of foreign body | Volume | Easiness of swallowing | Disintegration |
|---|---|---|---|---|---|---|
| Com. Ex. 3 | 4.11 | Amount of granules on 710 μm 0%<br>Amount of granules on 600 μm 20%<br>Amount of granules on 500 μm 70%<br>Amount of granules on 400 μm 95%<br>Amount of granules on 355 μm 100%<br>bulk density 0.51 g/mL | ◯ | Δ | Δ | ⊙ |

From the above, it has been clarified that granules having a bulk density of not less than 0.57 g/mL, especially not less than 0.59 g/mL, particularly not less than 0.62 g/mL, are preferable, and granules having a particle size distribution wherein granules in a preparation have the maximum particle size of not more than 1000 μm, particularly not more than 710 μm, are preferable.

Industrial Applicability

The amino acid-containing granule preparation of the present invention comprises granules having a maximum particle size of substantially not more than 1000 μm and a bulk density of not less than 0.57 g/mL, and therefore, can reduce the volume thereof. As a result, since the amino acid-containing granule preparation of the present invention can be taken without an uncomfortable feeling and a sensation of foreign body, it can enhance medication compliance. While the amino acid-containing granule preparation of the present invention is consolidated to reduce its volume, it disintegrates rapidly.

This application is based on patent application Nos. 2007-199875 (filing date: Jul. 31, 2007), 2007-279550 (filing date: Oct. 26, 2007) and 2008-155594 (filing date: Jun. 13, 2008), filed in Japan, the contents of which are incorporated in full herein by this reference.

The invention claimed is:

1. A granule preparation comprising:
granules comprising an amino acid comprising isoleucine, leucine and valine, wherein the granules have a particle size distribution such that an amount of granules on an aperture 355 μm sieve is 100% and an amount of granules on an aperture 710 μm sieve is 0%, and the granules have a bulk density of not less than 0.59 g/mL and not more than 0.75 g/mL,
wherein a weight ratio of isoleucine, leucine and valine is 1:1.5-2.5:0.8-1.7.

2. A pharmaceutical product or food, comprising 1-10 g of the granule preparation of claim 1 per one ingestion dose.

3. The granule preparation of claim 1, wherein the bulk density is not less than 0.62 g/mL and not more than 0.75 g/mL.

4. The granule preparation of claim 1, wherein the weight ratio of isoleucine, leucine and valine is 1:1.9-2.2:1.1-1.3.

5. A granule preparation comprising:
granules comprising isoleucine, leucine and valine,
wherein the granules have a particle size distribution such that an amount of granules on an aperture 355 μm sieve is 100% and an amount of granules on an aperture 710 μm sieve is 0%, and the granules have a bulk density of not less than 0.59 g/ml and not more than 0.75 g/ml, a weight ratio of isoleucine, leucine and valine is 1:1.5-2.5:0.8-1.7, and the granules are produced by a method comprising preparing the granules comprising isoleucine, leucine and valine, sieving the granules, and optionally milling the granules.

6. The granule preparation of claim 5, wherein the granules have a particle size distribution such that an amount of granules on an aperture 400 μm is 94%.

7. The granule preparation of claim 1, wherein the granules have a particle size distribution such that an amount of granules on an aperture 400 μm is 94%.

8. The granule preparation of claim 1, wherein the granules have a particle size distribution such that an amount of granules on an aperture 500 μm is 70%.

9. The granule preparation of claim 5, wherein the granules have a particle size distribution such that an amount of granules on an aperture 500 μm is 70%.

* * * * *